(12) United States Patent
Schledjewski et al.

(10) Patent No.: US 6,524,712 B1
(45) Date of Patent: Feb. 25, 2003

(54) FLEXIBLE MULTILAYER FILM

(75) Inventors: Ralf Schledjewski, Kaiserslautern (DE); Antoine Cassel, Walsrode (DE); Rainer Brandt, Walsrode (DE); Aileen Craig, Bomlitz (DE)

(73) Assignee: Wolff Walsrode AG, Walsrode (DE)

( * ) Notice: Subject to any disclaimer, the term of this patent is extended or adjusted under 35 U.S.C. 154(b) by 0 days.

(21) Appl. No.: 09/826,186

(22) Filed: Apr. 4, 2001

(30) Foreign Application Priority Data

Apr. 10, 2000 (DE) .......................................... 100 17 817

(51) Int. Cl.$^7$ ............................................... B32B 27/00
(52) U.S. Cl. ................ 428/423.1; 428/423.3; 428/423.7
(58) Field of Search ........................... 428/423.1, 423.3, 428/423.7

(56) References Cited

U.S. PATENT DOCUMENTS 4,868,058 A    9/1989  Biglione et al. ............ 428/412
5,843,539 A  * 12/1998  Harvey et al. .......... 156/244.11
6,312,825 B1 * 11/2001  Su et al. ................. 264/173.15

FOREIGN PATENT DOCUMENTS

| CA | 2123053 | 11/1994 |
| EP | 963760 A1 * | 6/1980 |
| EP | 365211 | 4/1990 |
| EP | 699520 | 3/1996 |

* cited by examiner

*Primary Examiner*—Terressa M. Boykin
(74) *Attorney, Agent, or Firm*—Godfreid R. Akorli; James R. Franks

(57) ABSTRACT

A multilayer film is described which has at least one first layer (1) of thermoplastic polyurethane, at least one second layer (2) of thermoplastic elastomer, and optionally a third layer (3) of thermoplastic polyurethane. The ratio of the water vapor permeability level of the first layer (1) to the water vapor permeability level of the second layer (2), of the multilayer film is at least two. When the optional third layer (3) is present in the multilayer film, the first and third layers enclose the second layer. Also described are filled articles (e.g., water beds and hot/cold pads), which are fabricated from the multilayer films of the present invention.

10 Claims, No Drawings

FLEXIBLE MULTILAYER FILM

FIELD OF THE INVENTION

The present invention relates to resilient thermoplastic multilayer films having at least two layers. The multilayer films of the present invention have at least one first layer (1) of thermoplastic polyurethane, and at least one second layer (2), which is formed from a thermoplastic elastomer with low water vapor permeability. The combination of at least one layer of thermoplastic urethane polymer and at least one layer of a thermoplastic elastomer results in a flexible multilayer film having a good mechanical property profile and a very good water vapor barrier effect.

BACKGROUND OF THE INVENTION

Flexible films with good mechanical properties are required for the production of flexible filled articles filled with gaseous or liquid media, such as water beds, for example. It is known that such applications may be served by films of plasticised PVC. Given the specific properties of PVC, a relatively large amount of material has to be typically used.

It is additionally known that thermoplastic polyurethanes are used for producing flexible containers for gaseous or liquid media. Of advantage here is the high mechanical property level, whereby relatively small wall thicknesses may be achieved. A problem is the high diffusion coefficient for polar media such as water vapor, for example.

Single-layer films of thermoplastic polyurethanes (TPE-U), processes for the production thereof and the use thereof are known according to the prior art for example from EP-A-0 308 683, EP-A-0 526 858, EP-A-0 571 868 or EP-A-0 603 680. The structures described in these specifications may be incorporated into laminating films as a higher melting-point layer or layers for multilayer films or are already incorporated into the laminating films known in the art. The production of TPE-U films using substantially incompatible polymers as flatting agents in TPE-U is also described, e.g., in DE-A 41 26 499.

Multilayer, coextruded films of TPE-U and other raw materials assigned to the thermoplastics group have also been described. In addition to coextrusion with polyolefinic thermoplastics, in which the polyolefinic layer does not as a rule undergo any interlayer adhesion with regard to the TPE-U layer and merely exhibits the function of a supporting or separating layer, multilayer structures with good interlayer adhesion are also known. EP-A-0 842 768 describes, for example, a multilayer structure of TPE-U and a polyolefinic coupling agent. In the case of such structures, cracking occurs in the thermoplastic layer as a result of the low elasticity of the thermoplastics in the event of relatively frequent cyclic loads with high strain values, thereby resulting in functional impairment.

In addition to thermoplastic polyurethanes, there exist further flexible materials which are generally covered collectively by the generic term thermoplastic elastomers (TPE). Of primary importance among the groups suitable for film processing are block copolymers. These include, in addition to TPE-U, styrene-based systems (TPE-S), polyether ester types (TPE-E) and polyether block amides (TPE-A). Films based on TPE-E are described for example in U.S. Pat. No. 5,859,083, wherein particular emphasis is placed therein on high water vapor permeability. The same applies to the films of TPE-A described in EP-A-0 761 715. TPE-S suitable for films and the use thereof are described in DE-A-1 9628 834, for example. An overview of the thermoplastic elastomer group is given for example in: Thermoplastic elastomers: a comprehensive review, ed. N. R. Legge, G. Holden and H. E. Schroeder, Carl Hanser Verlag, Munich 1987 and Thermoplastische Elastomere—Herausforderung an die Elastomerverarbeiter, ed.: VDI-Gesellschaft Kunststofftechnik, VDI Verlag, Düsseldorf, 1997.

SUMMARY OF THE INVENTION

The object was thus to provide a flexible film with a mechanical property profile superior to that of plasticised PVC combined with high water vapor impermeability. To minimize production costs, the combination of properties should, where possible, be obtained in a single-stage process.

In accordance with the present invention, there is provided a multilayer film comprising:
 at least one first layer (1) of thermoplastic polyurethane;
 at least one second layer (2) of thermoplastic elastomer; and
 optionally a third layer (3) of thermoplastic polyurethane (which may be the same or different than the thermoplastic polyurethane of the first layer),
wherein the ratio of the water vapor permeability level of said first layer (1) to the water vapor permeability level of said second layer (2) is at least two, and when said optional third layer (3) is present, said first (1) and third (3) layers together enclose said second layer (2).

Other than in the operation examples, or where otherwise indicated, all numbers expressing quantities of ingredients, reaction conditions, and so forth used in the specification and claims are to be understood as modified in all instances by the term "about."

DETAILED DESCRIPTION OF THE INVENTION

Surprisingly, the water vapor permeability of the multilayer film of the present invention are very low. If the ratio of the water vapor permeabilities of the layers (1) and (2) is increased to at least six, the water vapor permeability of the multilayer films of the present invention may be further minimized. Therefore, in a preferred embodiment of the multilayer film of the present invention, the ratio of the water vapor permeability level of the first layer (1) to the water vapor permeability level of the second layer (2) is at least six.

The first layer (1) and optional third layer (3) of the multilayer film of the present invention are each independently composed of at least one thermoplastic polyurethane elastomer, preferably of a predominantly linear thermoplastic polyurethane elastomer, the relatively long chain diol component of which is a polyester diol or polyether diol and which exhibits a Shore-A hardness of 70–95, preferably 85–95, as determined in accordance with DIN 53,505.

Suitable thermoplastic polyether/ or polyester/ polyurethane elastomers and/or mixtures thereof may for example be produced by art-recognized batch and/or partially and/or fully continuous processes, in particular by the reaction in a screw extruder of the following components a) through e).

a) organic, preferably aromatic or cycloaliphatic diisocyanates;
 b) polymeric diols with molecular weights of preferably 500 to 8000;

c) chain-extending components with molecular weights of preferably 60 to 400;

d) optionally in the presence of catalysts; and e) optionally in the presence of auxiliary substances and/or additives.

Components a) through e) which may be used in the production of suitable thermoplastic polyether/ or polyester/ polyurethane elastomers and/or mixtures thereof are described in further detail as follows.

a) The organic diisocyanates (a) preferably comprise aromatic or cycloaliphatic diisocyanates. In detail, the following may be mentioned by way of example: aromatic diisocyanates, such as 2,4- and 2,6-tolylene diisocyanate, 4,4'-, 2,4'- and 2,2'-diphenylmethane diisocyanate or mixtures thereof, cycloaliphatic diisocyanates, such as isophorone diisocyanate, 1,4-cyclohexane diisocyanate and 4,4'-, 2,4'- and 2,2'-dicyclohexylmethane diisocyanate or mixtures thereof.

b) Suitable higher molecular weight diol compounds (b) with preferred molecular weights of 400 to 8000 are preferably molecules of linear structure with a low glass transition temperature or softening point. These include polyetherols and polyesterols. However, hydroxyl group-containing polymers, for example polyacetals such as polyoxymethylenes and in particular water-insoluble formals and aliphatic polycarbonates, in particular those from diphenyl carbonate and 1,6-hexanediol, produced by transesterification, are also worthy of consideration. Moreover, hydroxyl group-capped diol compounds of polyolefins, in particular aliphatic hydroxyl group-capped copolymers of ethylene and butylene are also feasible. The diol compounds have to be at least predominantly linear, i.e. of difunctional structure for the purposes of the isocyanate reaction. The above-mentioned diol compounds may be used as individual components or in the form of mixtures.

c) The chain-extending agents with molecular weights of 60 to 400, preferably 60 to 300, may preferably comprise alkane diols with 2 to 12 carbon atoms, preferably with 2, 4 or 6 carbon atoms, such as for example ethanediol, 1,6-hexanediol and in particular 1,4-butanediol, and dialkylene ether glycols, such as for example diethylene glycol and dipropylene glycol. However, diesters of terephthalic acid with alkanediols having 2 to 4 carbon atoms are also suitable, such as for example terephthalic acid bis-ethanediol or -1,4-butanediol, hydroxyalkylene ethers of hydroquinone, (cyclo-)aliphatic diamines, such as for example isophoronediamine, ethylenediamine, and aromatic diamines, such as for example 2,4- and 2,6-tolylenediamine.

d) Suitable catalysts, which accelerate in particular the reaction between the isocyanate groups of category a) and the hydroxyl groups of categories b) and c), are the conventional tertiary amines that are well known to those of ordinary skill in the art, such as for example triethylamine, dimethylcyclohexylamine, N-methylmorpholine, N,N'-dimethylpiperazine, 2-(dimethylaminoethoxy)ethanol, diazabicyclo(2,2,2) octane and the like, together with in particular organic metal compounds such a titanic acid esters, iron compounds such as for example iron(III) acetylacetonate, tin compounds, such as tin diacetate, tin dioctoate, tin dilaurate or the tin dialkyl salts of aliphatic carboxylic acids such as dibutyltin diacetate, dibutyltin dilaurate or the like. The catalysts are conventionally used in amounts of from 0.001 to 0.2 parts per 100 parts of hydroxyl compound b).

e) In addition to catalysts, auxiliary substances and/or additives e) may also be added to the structural components a) to c). Examples of auxiliary substances and/or additives that may be used include, but are not limited to, lubricants, inhibitors, stabilizers acting with regard to hydrolysis, light, heat, oxidation or discoloration, dyestuffs, pigments, inorganic and/or organic fillers, reinforcing agents and low molecular weight plasticisers.

Suitable thermoplastic polyurethanes that may be used in the present invention include commercially available thermoplastic polyurethanes. Examples of commercially available thermoplastic polyurethanes that may be used in the present invention include, but are not limited to, those available under the trademarks DESMOPAN thermoplastic polyurethane, ELASTOLLAN thermoplastic polyurethane, ESTANE thermoplastic polyurethane, MORTHANE thermoplastic polyurethane, PELLETHANE thermoplastic polyurethane, PEARLTHANE thermoplastic polyurethane, SKYTHANE thermoplastic polyurethane, TECOFLEX thermoplastic polyurethane, and TEXIN thermoplastic polyurethane.

In a particularly suitable embodiment, the multilayer films according to the present invention comprise resilient urethane/elastomer formulation components, the soft segment phase of which consists predominantly of ether soft segment structural units. In this way, better resistance to hydrolysis is achieved. In addition, such materials exhibit better resistance to fungal and microbial attack.

To produce the second layer (2), thermoplastic elastomers are preferably used which exhibit a water vapor permeability level which lies between 0 and 150 $g/cm^2*d$, as determined in accordance with DIN 53,122, using a 50 $\mu$m thick layer of the film, at 23° C., and 85% relative humidity. In a particularly preferred embodiment of the multilayer film according to the present invention, the thermoplastic elastomer used to produce the second layer (2) exhibits a water vapor permeability level of between 0 and 50 $g/cm^2*d$, as determined in accordance with DIN 53,122, using a 50 $\mu$m thick layer of the film, at 23° C., and 85% relative humidity. In a yet more preferred embodiment of the multilayer film according to the present invention, the thermoplastic elastomer used to produce the second layer (2) exhibits a water vapor permeability level of between 0 and 20 $g/cm^2*d$, preferably between 0.25 and 20 $g/cm^2$, as determined in accordance with DIN 53,122, using a 50 $\mu$m thick layer of the film, at 23° C., and 85% relative humidity.

In a particularly preferred embodiment, styrene-based thermoplastic elastomers (TPE-S) are used in the second layer (2) of the multilayer film according to the present invention.

The TPE-S used according to the present invention consist of alternating blocks or segments, which comprise styrene monomer-based units, also known as hard segments, and softer, rubber-like units or so-called soft segments. The individual blocks conventionally consist of at least one hundred monomer units. Linear triblock structures comprising styrene/soft segment/styrene blocks are widely used. Linear, star-shaped and branched structures also exist which are based on individual or repeatedly incorporated blocks of the type comprising n styrene/soft segment blocks, where n is greater than or equal to 1.

In an embodiment of the multilayer films according to the present invention, the first layer (1), second layer (2) and optional third layer (3) each independently contain additional conventional additives selected from:

I. antiblocking agents, inorganic or organic spacers;

II. lubricants or mould-release agents;

III. pigments or fillers; and

IV. stabilizers.

The total content of the additives I through IV is preferably between 0% and 30% by weight, based on the total weight of the layer. The conventional additives which may be contained in the multilayer films according to the present invention are described by Gächter and Müller, for example, in: Kunststoff-Additive, Carl Hanser Verlag Munich, 3$^{rd}$ edition (1989).

In a particularly preferred embodiment of the present invention, the multilayer film comprises an at least three-layer structure, characterized in that the second layer (2) containing the thermoplastic elastomer, lies between and is enclosed by at least one first layer (1) and at least one third layer (3) each independently composed of thermoplastic polyurethane.

Multilayer films preferred according to the present invention have a total thickness of between 50 μm and 600 μm. In such a preferred multilayer film, the thickness of the first layer (1) and optional third layer (3) of thermoplastic polyurethane is preferably and independently between 20 μm and 400 μm, while the thickness of the TPE second layer (2) is preferably between 10 μm and 200 μm.

Of particular suitability for producing the multilayer film according to the present invention are the art-recognized thermoforming processes for processing plastics to yield multilayer sheet products. An example of which includes, production by coextrusion, which preferably proceeds by the blown film process. Of the production processes suitable for producing multilayer thermoplastic sheet products, coextrusion is particularly preferred as a result of the better interlayer adhesion which may be achieved.

The surface properties of one or both sides of the multilayer films of the present invention may be modified using known physical and/or chemical treatment methods, such as for example corona treatment.

In accordance with a further embodiment of the present invention, there are provided filled articles (e.g., closed filled articles like welded bladders) comprising or fabricated from the multilayer films of the present invention as described previously herein, wherein the filling material may be either liquid or gaseous. Such filled articles are particularly suitable for accommodating water. Production of the filled articles proceeds using art-recognized joining process, such as for example high-frequency welding. Examples of filled articles according to the present invention, which comprise the multilayer films of the present invention include, but are not limited to water beds and hot/cold pads. The present invention is more particularly described in the following examples, which are intended to be illustrative only, since numerous modifications and variations therein will be apparent to those skilled in the art. Unless otherwise specified, all parts and percentages are by weight.

EXAMPLES

The films described in the following Examples and Comparative Examples were produced by blown film coextrusion. The structure of the screw extruders suitable for fusing thermoplastic resins is described for example by Wortberg, Mahlke and Effen in: Kunststoffe, 84 (1994) 1131–1138, by Pearson in: Mechanics of Polymer Processing, Elsevier Publishers, New York, 1985 or Davis-Standard in: Paper, Film & Foil Converter 64 (1990), pp. 84–90. Dies for shaping the melts into films are described inter alia by Michaeli in: Extrusions-Werkzeuge, Hanser Verlag, Munich 1991. The multilayer film of Example 1 is in accordance with the multilayer films of the present invention. Examples 2, 3 and 4 are Comparative Examples.

Example 1

Using a two-layer blown film die, a multilayer film according to the present invention was produced whose first layer (1) consisted of an ether TPE-U of Shore-A hardness 87, measured in accordance with DIN 53,505, corresponding to a Shore-D hardness of 36. Spacers in an amount of 2% by weight and 0.5% by weight waxes were added as additives to this 100 μm thick first layer (1). All the components used for this layer were melted together in an extruder.

The 100 μm thick second layer (2) was produced from a TPE-S. The TPE-S used here was a styrene/butadiene/styrene block copolymer of Shore-A hardness 85, measured in accordance with DIN 53,505, corresponding to a Shore-D hardness of 30.

The extrusion equipment was operated at temperatures of between 170° C. and 200° C. The two melt streams were superposed in a two-layer film blowing head with a processing temperature of 200° C. and discharged through an annular die with a diameter of 150 mm. By blowing with air, the annular melt web was cooled, then collapsed, separated and wound up.

Example 2

Using a three-layer blown film extruder, a comparative multilayer film was produced having two outer layers (1') and (3'), which enclosed a layer (2'). The two outer 75 μm thick layers (1') and (3') of the comparative multilayer film consisted of an ether TPE-U of Shore-A hardness 87, measured in accordance with DIN 53,505, corresponding to a Shore-D hardness of 36. Spacers in an amount of 4% by weight and 1% by weight waxes were added as additives to these 75 μm thick layers. All the components used for these layers were melted together in an extruder.

The 50 μm thick layer (2') of the comparative multilayer film was made from a coupling component. The coupling component comprised a copolymer of ethylene and maleic anhydride with a maleic anhydride content of less than 5 wt. %. The hardness of this component used to constitute the coupling layer was approximately Shore-A 67, measured in accordance with DIN 53,505, corresponding to approximately Shore-D 15.

The extrusion equipment was operated at temperatures of between 160° C. and 200° C. The three melt streams were superposed in a three-layer film blowing head with a processing temperature of 195° C. and discharged through an annular die with a diameter of 130 mm. By blowing with air, the annular melt web was cooled, then collapsed, separated and wound up.

Example 3

Using a single-layer blown film die, a comparative film was produced whose single layer (1") consisted of an ether TPE-U of Shore-A hardness 87, measured in accordance with DIN 53,505, corresponding to Shore-D hardness of 36. Spacers in an amount of 2% by weight and 0.3% waxes by weight were added as additives to this single 200 μm thick layer. All the components used for this layer were melted together in an extruder.

The extrusion equipment was operated at temperatures of between 170° C. and 200° C. The melt stream was discharged at a processing temperature of 200° C. through an annular die with a diameter of 150 mm. By blowing with air, the annular melt web was cooled, then collapsed, separated and wound up.

Example 4

Using a single-layer blown film die, a comparative film was produced whose single layer (1''') consisted of a styrene/butadiene/styrene block copolymer of Shore-A hardness 85, measured in accordance with DIN 53,505, corresponding to a Shore-D hardness of 30.

The extrusion equipment was operated at temperatures of between 170° C. and 200° C. The melt stream was discharged at a processing temperature of 195° C. through an annular die with a diameter of 150 mm in a layer thickness of 100 μm. By blowing with air, the annular melt web was cooled, then collapsed, separated and wound up.

The films of Examples 1 through 4 were evaluated as follows. All four films were characterized with regard to water vapor permeability, measured in accordance with DIN 53,122, at 23° C., and 85% relative humidity; and mechanical load-carrying capacity, measured in accordance with DIN EN ISO 527 (tensile test) and DIN 53 515 (tear propagation resistance). Both multilayer films (Example 1 and Example 2) were assessed for interlayer adhesion, as determined in accordance with DIN 53,357 Method B, when fresh and after the application of fatigue stress. The fatigue stress was applied by dynamic cyclic loading with a strain amplitude of 50% over 10,000 cycles. The results of the evaluation of the films of Examples 1 through 4 are summarized in the following Table 1.

TABLE 1

|  | Example 1 | Example 2 | Example 3 | Example 4 |
| --- | --- | --- | --- | --- |
| Thickness (μm) | 195 | 195 | 205 | 100 |
| Water vapor permeability DIN 53,122 at 23° C./ 85% relative humidity (g/m² · d) | 11 | 8.2 | 132.5 | 20 |
| Breaking stress DIN EN 120 527 (Mpa) | 44.9 | 48.5 | 54.3 | 28 |
| Elongation at break DIN EN ISO 527 (%) | 723 | 858 | 823 | 605 |
| Tear propagation resistance DIN 53,515 (N/mm) | 51.7 | 42 | 55.2 | 32 |
| Interlayer adhesion (fresh) DIN 53,357 Method B (N/15 mm) | >10 | 6.13 | —[(1)] | — |
| Interlayer adhesion after fatigue stress DIN 53,357 Method B (N/15 mm) | >10 | 0 | — | — |

[(1)]The symbol "—" in Table 1 means "Not Applicable."

The results summarized in Table 1 clearly indicate that a marked reduction in water vapor permeability is achieved by the multilayer film structure of the invention as represented by Example 1, the water vapor permeability being capable of non-linear derivation from the water vapor permeabilities of the individual layers (Example 3 and Example 4). At the same time, the mechanical properties are kept at a high level. Example 2 shows that, when materials not according to the present invention, here a thermoplastic coupling agent, are used in the layer (2'), marked deficiencies in the long-term properties result.

Although the invention has been described in detail in the foregoing for the purpose of illustration, it is to be understood that such detail is solely for that purpose, and that variations can be made therein by those skilled in the art without departing from the spirit and scope of the invention except as it may be limited by the following claims.

What is claimed is:

1. A multilayer film consisting essentially of:
   at least one first layer of thermoplastic polyurethane;
   at least one second layer of styrene-based thermoplastic elastomer having alternating hard segments and soft segments; and
   optionally a third layer of thermoplastic polyurethane,
   wherein the ratio of the water vapor permeability level of said first layer to the water vapor permeability level of said second layer is at least two, and when said optional third layer is present, said first and third layers enclose said second layer.

2. The multilayer film of claim 1, wherein the ratio of the water vapor permeability level of said first layer to the water vapor permeability level of said second layer, is at least six.

3. The multilayer film of claim 1, wherein the water vapor permeability of said second layer is between 0 and 150 g/cm²*d, as determined in accordance with DIN 53 122, using a 50 μm thick layer of the film, at 23° C. and 85% relative humidity.

4. The multilayer film of claim 1, wherein the water vapor permeability of said second layer is between 0 and 50 g/cm²*d, as determined in accordance with DIN 53 122, using a 50 μm thick layer of the film, at 23° C. and 85% relative humidity.

5. The multilayer film of claim 1, wherein the water vapor permeability of said second layer is between 0 and 20 g/cm²*d, as determined in accordance with DIN 53 122, using a 50 μm thick layer of the film, at 23° C. and 85% relative humidity.

6. The multilayer film of claim 1, wherein the thermoplastic polyurethane of said first layer has a soft segment formed substantially by ether groups.

7. The multilayer film of claim 1, wherein the composition of said third layer is substantially the same as the composition of said first layer.

8. The multilayer film of claim 1, wherein said multilayer film has a total thickness of between 50 μm and 600 μm, the thickness of each of said first layer and said optional third layer is independently between 20 μm and 400 μm, and the thickness of said second layer of thermoplastic elastomer is between 10 μm and 200 μm.

9. A filled article comprising the multilayer film of claim 1.

10. The multilayer film of claim 1 wherein said styrene-based thermoplastic elastomer is a styrene/butadiene/styrene block copolymer.

* * * * *